United States Patent
Hahm et al.

(10) Patent No.: US 6,800,727 B2
(45) Date of Patent: Oct. 5, 2004

(54) PEPTIDES WITH INCREASED + CHARGE AND HYDROPHOBICITY BY SUBSTITUTING ONE OR MORE AMINO ACIDS OF CA-MA PEPTIDE AND PHARMACEUTICAL COMPOSITIONS CONTAINING THEREOF

(75) Inventors: Kyung-Soo Hahm, Seoul (KR); Dong Gun Lee, Taejon-si (KR); YoonKyung Park, Jeollanam-do (KR)

(73) Assignee: Chosun University (KR)

( * ) Notice: Subject to any disclaimer, the term of this patent is extended or adjusted under 35 U.S.C. 154(b) by 0 days.

(21) Appl. No.: 10/081,418

(22) Filed: Feb. 22, 2002

(65) Prior Publication Data

US 2003/0096745 A1 May 22, 2003

(30) Foreign Application Priority Data

Sep. 19, 2001 (KR) ........................................ 2001-57837

(51) Int. Cl.[7] ........................ A61K 38/00; A61K 39/00; A01N 37/18; C07K 14/00; C07K 2/00
(52) U.S. Cl. ........................ 530/300; 530/324; 530/327; 424/184.1; 424/192.1; 424/185.1; 514/2
(58) Field of Search ................................ 530/300, 324, 530/327; 424/184.1, 192.1, 185.1; 514/2

(56) References Cited

U.S. PATENT DOCUMENTS

| | | | |
|---|---|---|---|
| 5,792,831 A | * | 8/1998 | Maloy |
| 6,642,203 B1 | * | 11/2003 | Destoumieux et al. |
| 2003/0083243 A1 | * | 5/2003 | Owen |
| 2003/0096745 A1 | * | 5/2003 | Hahm et al. |
| 2003/0232750 A1 | * | 12/2003 | Krieger et al. |
| 2004/0019181 A1 | * | 1/2004 | Falla et al. ................. 530/324 |
| 2004/0023884 A1 | * | 2/2004 | Little ........................... 514/12 |

FOREIGN PATENT DOCUMENTS

| | | | |
|---|---|---|---|
| EP | 0299828 | * | 1/1989 |
| WO | WO 95/01095 | * | 1/1995 |
| WO | WO 95/27497 | * | 10/1995 |

OTHER PUBLICATIONS

Shin et al, Brochem. & Mol. Biol. Int. 44/6:1119–1126, May 1998.*
Lee et al, J. Biochem. Mol. Biol. & Biophys. 2:243–248, 1999.*
Shin et al, J. Biochem. Mol. Biol. & Biophys. 4:135–45, 2000.*
Oh et al, Biochemistry, 39: 11855–11864, 2000.*
Kang et al, J. Peptide Research, 52:45–50, 1998.*
Shin et al, J. Peptide Research, 53:82–90, 1999.*
Shin et al, J. Peptide Research, 50:279–285, 1997.*
Oh et al, J. Peptide Research, 53:578–89, 1999.*
Kim et al, Biotechnology Letters, 24:347–353, 2002.*
Boman et al, FEBS Letters, 259/1:103–106, Dec. 1989.*
Zasloff, PNAS, USA, 84:5449–5453, Aug. 1987.*
Steiner et al, Nature, 292:246–248, Jul. 1981.*
Lee et al, J. Microbiol & Biotechnol, 7/1:49–51, 1997.*
Shin et al, J. Biochem. Mol. Biol. 29/6:545–48, 1996.*
Song, Yub Shin et al. "Effects of the hinge region of cecropin A(1–8)–magainin 2(1–12), a synthetic antimicrobial peptide, on liposomes, bacterial and tumor cell" Biochemica et Biophysica Acta 1463 (2000) 209–218.
Song, Yub Shin et al. "Cecropin A—Magainin 2 Hybrid Peptides Having Potent Antimicrobial Activity With Low Hemolytic Effect" vol.44, No. 6, May 1998, Biochemistry and Molecular Biology International pp. 1119–1126.

* cited by examiner

Primary Examiner—Nita Minnifield
(74) Attorney, Agent, or Firm—Muserlian, Lucas and Mercanti

(57) ABSTRACT

The present invention relates to novel peptides with increased + charge and hydrophobicity by substituting one or more amino acids of CA-MA peptide in which cecropin A (CA) and magainin 2(MA) were conjugated and pharmaceutical compositions containing thereof. More precisely, the present invention relates to synthetic peptides prepared by substituting one or more amino acids of CA-MA peptide represented by the SEQ. ID. NO: 1 with amino acids having + charge and hydrophobicity and anti-bacterial, anti-fungal and anticancer compositions containing thereof. The synthetic peptides of the present invention have no cytotoxicity but have excellent anti-bacterial, anti-fungal and anticancer activity, leading in an effective use thereof as a safe anticancer agent and antibiotics.

7 Claims, 6 Drawing Sheets

Figures

SEQUENCE LISTING

```
<160> NUMBER OF SEQ ID NOS: 2

<210> SEQ ID NO 1
<211> LENGTH: 20
<212> TYPE: PRT
<213> ORGANISM: Artificial Sequence
<220> FEATURE:
<223> OTHER INFORMATION: CA-MA peptide made by fusing 1-8 amino acid of
      secropin A and 1-12 amino acid of magainin 2

<400> SEQUENCE: 1

Lys Trp Lys Leu Phe Lys Lys Ile Gly Ile Gly Lys Phe Leu His Ser
 1               5                  10                  15

Ala Lys Lys Phe
            20

<210> SEQ ID NO 2
<211> LENGTH: 20
<212> TYPE: PRT
<213> ORGANISM: Artificial Sequence
<220> FEATURE:
<223> OTHER INFORMATION: peptide with increased + charge and
      hydrophobicity by substituting amino acids of SEQ. ID. NO 1 with
      lysine and leucine

<400> SEQUENCE: 2

Lys Trp Lys Lys Leu Leu Lys Lys Pro Pro Pro Leu Leu Lys Lys Leu
 1               5                  10                  15

Leu Lys Lys Leu
            20
```

PEPTIDES WITH INCREASED + CHARGE AND HYDROPHOBICITY BY SUBSTITUTING ONE OR MORE AMINO ACIDS OF CA-MA PEPTIDE AND PHARMACEUTICAL COMPOSITIONS CONTAINING THEREOF

This patent application claims priority from KO-2001-0057837, the disclosure of which is incorporated by reference herein in its entirety.

FIELD OF THE INVENTION

The present invention relates to novel peptides with increased + charge and hydrophobicity by substituting one or more amino acids of CA-MA peptide in which cecropin A (CA) and magainin 2 (MA) were conjugated and pharmaceutical compositions containing thereof. More precisely, the present invention relates to synthetic peptides prepared by substituting one or more amino acids of CA-MA peptide represented by the SEQ. ID. NO: 1 with amino acids having + charge and hydrophobicity and anti-bacterial, anti-fungal and anticancer compositions containing thereof. The synthetic peptides of the present invention have no cytotoxicity but have excellent anti-bacterial, anti-fungal and anticancer activity, leading in an effective use thereof as a safe anti-cancer agent and antibiotics.

BACKGROUND

Bacteria infection is one of the most common but fatal causes for human diseases. Infection has been successfully treated by antibiotics, but the abuse of antibiotics brought another problem that bacteria now might have resistance against antibiotics. In fact, the speed which bacteria are adapting and having resistance against new antibiotics outruns that of developing new antibiotics analogues. For example, fatal *Enterococcus faecalis, Mycobacterium tuberculosis* and *Pseudomonas aeruginosa* are known to have raised their resistance against every possible antibiotics (Stuart B. Levy, *Scientific American*, 1998, 46–53).

Tolerance is different from resistance against antibiotics, and it was firstly found in Pneumococcus sp. in 1970s, which provided an important clue for disclosing the mechanism of penicillin (Tomasz, et al., *Nature*, 1970, 227, 138–140). Some bacteria species having tolerance stopped growing under the ordinary concentration of antibiotics but never died. Tolerance is caused by that the activity of autolytic enzyme of bacteria, like autolysin, is suppressed when the antibiotics inhibit cell wall synthetase. Penicillin can kill bacteria by activating endogenous hydrolytic enzyme; on the other hand, bacteria can survive by restraining the activity thereof even when being treated with antibiotics.

It is a clinical hot issue that bacteria are having tolerance against various antibiotics since infection cannot be effectively cured with antibiotics due to the tolerance (Handwerger and Tomasz, *Rev. Infec. Dis.*, 1985, 7, 368–386). Again, once bacteria have tolerance, they can have resistance, which helps that bacteria survive under antibiotics treatment. Such bacteria can acquire new genetic elements having resistance against antibiotics, thus they can grow even under antibiotics treatment. Actually, bacteria having resistance have tolerance, too (Liu and Tomasz, *J. Infect. Dis.*, 1985, 152, 365–372). Thus, it is urgent to develop novel antibiotics, which can kill antibiotics-resistant bacteria.

There are two types of tolerance in the aspect of its mechanism. The first one is phenotypic tolerance, which occurs when the growing speed decreases in all kinds of bacteria (Tuomanen E., *Revs. Infect. Dis.*, 1986, 3, S279–S291), and the second one is genotypic tolerance acquired by mutation in a certain type of bacteria. For both cases, down regulation of autolysin activation is basically occurring. In the case of phenotypic tolerance acquired by outside stimulus, down regulation takes place temporally while down regulation occurs permanently in the case of genotypic tolerance acquired by mutation, which cause the change of hemolysis regulating routes. Autolysin deficiency is believed to cause the simplest genotypic tolerance, but the bacteria having tolerance acquired by autolysin deficiency have not been reported yet. Such tolerance observed in clinics rather seemed to be caused by the regulation of autolysin activity (Tuomanen et al., *J. Infect. Dis.*, 1988, 158, 36–43).

In order to fight bacteria having tolerance against antibiotics, it is required to develop new antibiotics including one that is working separately from autolysin activity. In addition, it is also required to provide pharmaceutical compositions containing thereof to treat bacteria infection and inflammation effectively.

Meanwhile, bacteria can kill the neighboring bacteria by synthesizing peptides or small organic molecules, which are called bacteriocin. Such bacteriocins are classified into three groups according to their structure. The first group is lantibiotics, the second group is nonlantibiotics, and the third group is those, which are secreted by signal peptide (Cintas et al., *J. Bad.*, 1998, 180, 1988–1994). Animals including insects also produce naturally synthesized peptide antibiotics (Bevines et al., *Ann. Rev. Biochem.*, 1990, 59, 395–414), which are classified into three groups according to their structure as well. The first group is cysteine-rich β-sheet peptides, the second group is α-helical amphiphilic peptides, and the third group is proline-rich peptides (Mayasaki et al., *Int. J. Antimicrob. Agents*, 1998, 9, 269–280). Those anti-bacterial peptides are known to play an important role in host-defense and congenital immune system (Boman, H. G., *Cell*, 1991, 65, 205; Boman, H. G., *Annu. Rev. Microbiol.*, 1995, 13, 61). The anti-bacterial peptides have many different structures depending on amino acid sequences, and the most common structure is amphiphilic α-helical structure having no cysteine, just like cecropin, an anti-bacterial peptide found in insects.

Among those peptides, the anti-bacterial activity of amphiphilic peptides has been studied and the development of antibiotics using the amphiphilic peptides has been tried. As of today, magainin 2(MA), cecropin A (CA) and melittin (ME) have been reported as amphiphilic peptides.

Amphiphilic peptides of cecropin group were first found in a fruit fly and later in a silkworm pupa and in pig intestine. While cecropin A was reported to have high anti-bacterial activity but low anti-fungal and anticancer activity (Boman, H. G. and Hultmark, D., *Annu. Rev. Microbiol.*, 1987, 41, 103), magainin 2 was known not to have cytotoxic activity but to have appreciable anti-bacterial, anti-fungal, anticancer and anti-protozoa activity (Zasloff, M., *Proc. Natl. Acad. Sci. USA*, 1987, 84, 5449). It has been further reported that new synthetic peptides having excellent anti-bacterial, anti-fungal and anticancer activity could be prepared by constructing conjugated peptides by recombination from parts of the sequences of the above two peptides (Chan, H. C., et al., *FEBS Lett.*, 1989, 259, 103; Wade, D., et al., *Int. J. Pept. Prot. Res.*, 1992, 40, 429).

The present inventors have designed and synthesized novel peptides having amino acid sequences with + charge and hydrophobicity at amino terminal, taking amphiphilic peptide conjugated cecropin A and magainin 2 as a template. And the present invention has been accomplished by confirming that the synthetic peptides of the present invention could be effectively used as anticancer agents and antibiotics owing to their anti-bacterial, anti-fungal and anti-cancer activity.

SUMMARY OF THE INVENTION

It is an object of this invention to provide novel peptides and their derivatives with increased + charge and hydrophobicity by substituting one or more amino acids of cecropin A and magainin 2 conjugated CA-MA peptide represented by the SEQ. ID. NO: 1 and with excellent anti-bacterial, anti-fungal and anticancer activity without cytotoxicity.

It is another object of this invention to provide pharmaceutical compositions for anti-bacterial, anti-fungal and anti-cancer agent containing the above synthetic peptides.

Figure 1:
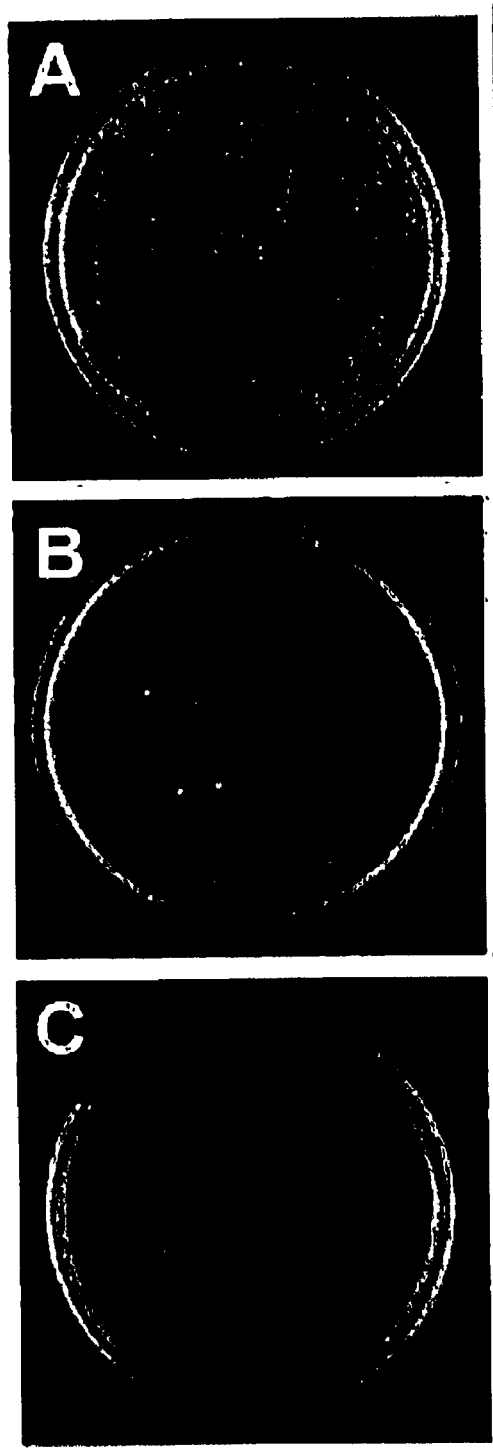
FIG. 1 is photographs showing the number of colonies on LB agar plate, in which *Bacillus subtilis* was treated with synthetic peptide of the present invention, A: Positive control, B: CA-MA peptide, C: Synthetic peptide represented by the SEQ. ID. NO: 2

A: Anticancer activity against Calu-6 cell line,

B: Anticancer activity against Jurkat cell line,

C: Anticancer activity against SNU 601 cell line,

●CA-MA peptide,

0: Synthetic peptide represented by the SEQ. ID. NO: 2

DETAILED DESCRIPTION OF PREFERRED EMBODIMENTS

To accomplish those objects, the present invention provides novel peptides and their derivatives with increased + charge and hydrophobicity by substituting one or more amino acids of cecropin A and magainin 2 conjugated CA-MA peptide represented by the SEQ. ID. NO:1.

The present invention also provides anti-bacterial, anti-fungal and anticancer pharmaceutical compositions containing the above peptides and their derivatives.

Hereinafter, the present invention is described in detail.

In one aspect, the present invention provides novel peptides and their derivatives with increased + charge and hydrophobicity by substituting one or more amino acids of cecropin A and magainin 2 conjugated CA-MA peptide represented by the SEQ. ID. NO: 1.

Peptides and their derivatives of the present invention were synthesized to have increased + charge and hydrophobicity by substituting a few amino acids including hinge region of CA-MA peptide which was prepared by conjugating 1–8 amino acid region of amphiphilic helical CA and 1–12 amino acid region of MA, and represented by the SEQ. ID. NO: 1, with other amino acids.

In order to prepare synthetic peptides of the present invention, the present inventors used Merrifield's liquid solid phase method in which Fmoc (9-fluorenylmethoxycarbonyl) was used as a protecting group (Merrifield, R. B., *J. Am. Chem. Soc.*, 1963, 85, 2149). Every synthetic peptide with increased + charge and hydrophobicity by substituting one or more amino acids including hinge region of CA-MA peptide represented by the SEQ. ID. NO: 1 could be peptide of the present invention. Especially, peptides and their derivatives prepared by substituting glysine-isoleucine-glycine residing at hinge region of CA-MA peptide represented by the SEQ. ID. NO: 1 with proline each, substituting $4^{th}$ leucine, $8^{th}$ isoleucine, $14^{th}$ leucine, $15^{th}$ histidine with lysine each, and substituting $5^{th}$ phenylalanine, $6^{th}$ lysine, $12^{th}$ lysine, $13^{th}$ phenylalnine, $16^{th}$ serine, $17^{th}$ alanine, $20^{th}$ phenylalanine with leucine were preferred.

The peptide synthesized as above was isolated and purified, after which the purity thereof was confirmed. As a result, the purity of the peptide was over 95%, and the molecular weight obtained by MALDI (Matrix-Assisted Laser Desorption Ionization) mass spectrometry (Hill, et al., *Rapid Commun. Mass Spectrometry*, 1991, 5, 395) was the same as the molecular weight obtained by calculation of amino acids. Therefore, it was confirmed that the peptide having correct amino acid sequence represented by the SEQ. ID. NO: 2 was synthesized.

The present invention also provides anti-bacterial, anti-fungal and anticancer pharmaceutical compositions containing the above peptides and their derivatives.

To confirm if the peptides and their derivatives of the present invention can be used for anti-bacterial, anti-fungal and anticancer agents, the present inventors have measured the anti-bacterial activity of the synthetic peptides by measuring minimal inhibitory concentration (referred as "MIC" hereinafter).

Synthetic peptide of the present invention represented by the SEQ. ID. NO: 2 was used to measure MIC value to each strain. As a result, synthetic peptide of the present invention was confirmed to have more than 4-fold anti-bacterial activity (varied a little depending on strains), comparing to the comparative group using CA-MA conjugation peptide (see Table 1).

Figure 2:
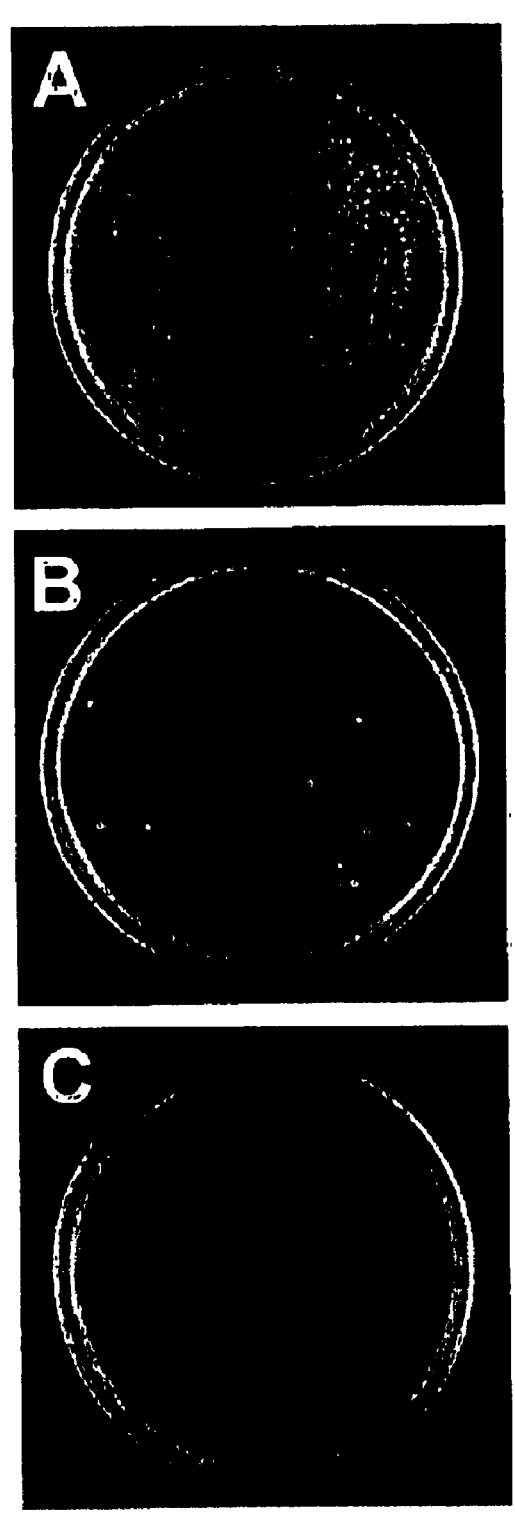
FIG. 2 is photographs showing the number of colonies on NB+0.5% NaCl agar plate, in which *Pseudomonas aeruginosa* was treated with synthetic peptide of the present invention, A: Positive control, B: CA-MA peptide, C: Synthetic peptide represented by the SEQ. ID. NO: 2

Also, anti-bacterial activity of the peptide of the present invention against *Bascillus subtilis* and *Pseudomonas aeruginosa* was measured on an LB agar plate. As a result, the synthetic peptide of the present invention represented by SEQ. ID. NO: 2 was confirmed to have remarkable anti-bacterial activity, compared to the CA-MA conjugation peptide (see FIG. 1 and FIG. 2).

Figure 3:
FIG. 3 is SEM (scanning electron microscopy) microphotographs showing the result of treating synthetic peptide of the present invention to *Bacillus subtilis*, A: Positive control, B: CA-MA peptide, C: Synthetic peptide represented by the SEQ. ID. NO: 2
Figure 3:
Figure 3:
Figure 4:
FIG. 4 is SEM microphotographs showing the result of treating synthetic peptide of the present invention to *Pseudomonas aeruginosa*, A: Positive control, B: CA-MA peptide, C: Synthetic peptide represented by the SEQ. ID. NO: 2
Figure 4:
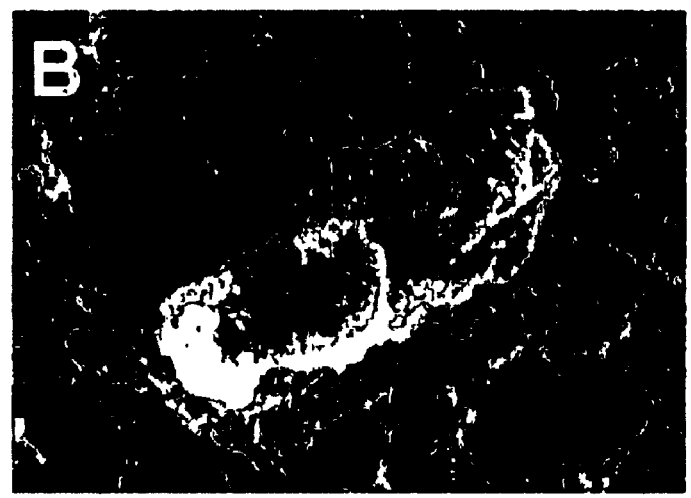
Figure 4:

In addition, observing the anti-bacterial activity of the CA-MA peptide of the present invention against *Bacillus subtilis* and *Pseudomonas aeruginosa* with scanning electron microscopy also supported the same result as above (see FIG. 3 and FIG. 4).

Again, the synthetic peptide of the present invention represented by SEQ. ID. NO: 2 was confirmed to have remarkable anti-bacterial activity compared to the CA-MA conjugation peptide, which resulted from observing the dynamic condition of lipid membrane after *Bacillus subtilis* and *Pseudomonas aeruginosa* were treated with the synthetic peptide (see FIG. 5).

In order to measure the anti-fungal activity of synthetic peptide of the present invention, the MIC values to *Candida albicans* and *Trichosporon beigelii* were measured by MTT assay method. As a result, the synthetic peptide of the present invention represented by the SEQ. ID. NO: 2 showed more than 2-fold anti-fungal activity comparing to the comparative group using CA-MA peptide (see Table 2).

In order to see if the synthetic peptide of the present invention have anticancer activity, human lung cancer cell line Calu-6, human stomach cell line SNU 601 and T-cell lymphoma cell line were treated with the peptide. As a result, the synthetic peptide of the present invention represented by the SEQ. ID. NO: 2 was confirmed to have higher anticancer activity than the comparative group using CA-MA peptide (see FIG. 6).

Further, the present inventors measured the hemolysis capacity of the synthetic peptide of the present invention in order to see if it has cytotoxicity. As a result, along with CA-MA peptide, the synthetic peptide of the present invention represented by the SEQ. ID. NO: 2 had no cytotoxicity. Meanwhile, melittin, bee venom, used as a positive control showed high cytotoxicity (see Table 3).

Considering all those results together, the synthetic peptide of the present invention represented by the SEQ. ID. NO: 2 was confirmed to have excellent anti-bacterial, anti-fungal and anticancer activity without cytotoxicity, so that the peptide can be effectively used as a safe anti-bacterial, anti-fungal and anticancer treatment agent.

Peptides and their derivatives of the present invention can be administered orally or parenterally. The compounds of the present invention can be prepared for oral or parenteral administration by mixing with generally-used fillers, extenders, binders, wetting agents, disintegrating agents, diluents such as surfactant, or excipients. The present invention also includes pharmaceutical formulations in dosage units. This means that the formulations are presented in the form of individual parts, for example tablets, coated tablets, capsules, pills, suppositories and ampules, the active compound content of which corresponds to a fraction or a multiple of an individual dose. The dosage units can contain, for example, 1, 2, 3 or 4 individual doses or ½, 1/3 or ¼ of an individual dose. An individual dose preferably contains certain amount of active compound, which is administered in one application and which usually corresponds to a whole, one half, one third, or a quarter of a daily dose. Non-toxic inert pharmaceutically suitable excipients are to be understood as solid, semi-solid or liquid diluents, fillers and formulation auxiliaries of all types. Preferred pharmaceutical formulations which may be mentioned are tablets, coated tablets, capsules, pills, granules, suppositories, solutions, suspensions and emulsions, pastes, ointments, gels, creams, lotions, dusting powders and sprays. Solid formulations for oral administration are tablets, pill, dusting powders and capsules. Liquid formulations for oral administrations are suspensions, solutions, emulsions and syrups, and the abovementioned formulations can contain various excipients such as wetting agents, sweeteners, aromatics and preservatives in addition to generally-used simple diluents such as water and liquid paraffin. Tablets, coated tablets, capsules, pills and granules can contain the active compound or compounds in addition to the customary excipients, such as (a) fillers and extenders, for example starches, lactose, sucrose, glucose, mannitol and silicic acid, (b) binders, for example carboxymethylcellulose, alginates, gelatine and polyvinylpyrrolidone, (c) humectants, for example glycerol, (d) disintegrating agents, for example agar-agar, calcium carbonate and sodium carbonate, (e) solution retarders, for example paraffin, and (f) absorption accelerators, for example quaternary ammonium compounds, (g) wetting agents, for example cetyl alcohol and glycerol monostearate, (h) adsorbents, for example kaolin and bentonite, and (i) lubricants, for example talc, calcium stearate, magnesium stearate, and solid polyethylene glycols, or mixtures of the substances listed under (a) to (i). The tablets, coated tablets, capsules, pills and granules can be provided with the customary coatings and shells, optionally containing opacifying agents, and can also be of a composition such that they release the active compound or compounds only or preferentially in a certain part of the intestinal tract, if appropriate in a delayed manner, examples of embedding compositions which can be used would be polymeric substances and waxes. If appropriate, the active compound or compounds can also be presented in microencapsulated form with one or more of the abovementioned excipients. Formulations for parenteral administration are sterilized aqueous solutions, water-insoluble excipients, suspensions, emulsions, and suppositories. Suppositories can contain, in addition to the active compound or compounds, the customary water-soluble or water-insoluble excipients, for example polyethylene glycols, fats, for example cacao fat, and higher esters (for example C14-alcohol with C16-fatty acid) or mixtures of these substances. Ointments, pastes, creams and gels can contain, in addition to the active compound or compounds, the customary excipients, for example animal and vegetable fats, waxes, paraffins, starch, tragacanth, cellulose derivatives, polyethylene glycols, silicones, bentonites, silicic acid, talc and zinc oxide, or mixtures of these substances. Dusting powders and sprays can contain, in addition to the active compound or compounds, the customary excipients, for example lactose, talc, silicic acid, aluminum hydroxide, calcium silicate and polyamide powder, or mixtures of these substances. Sprays can additionally contain the customary propellants, for example chlorofluorohydrocarbons. Solutions and emulsions can contain, in addition to the active compound or compounds, the customary excipients, such as solvents, solubilizing agents and emulsifiers, for example water, ethyl alcohol, isopropyl alcohol, ethylcarbonate, ethyl acetate, benzyl alcohol, benzyl benzoate, propylene glycol, 1,3-butylene glycol, dimethylformamide, oils, in particular cottonseed oil, groundnut oil, corn germ oil, olive oil, castor oil and sesame oil, glycerol, glycerol formal, tetrahydrofurfuyl alcohol, polyethylene glycols and fatty acid esters of sorbitan, or mixtures of these substances. For parenteral administration, the solutions and emulsions are also be in a sterile form which is isotonic with blood. Suspensions can contain, in addition to the active compound or compounds, the customary excipients, such as liquid diluents, for example water, ethyl alcohol and propylene glycol, and suspending agents, for example ethoxylated isostearyl alcohols, polyoxyethylene sorbitol and sorbitan esters, microcrystalline cellulose, aluminum metahydroxide, bentonite, agar-agar and tragacanth, or mixtures of these substances. The formulation forms mentioned can also contain coloring agents, preservatives and additives that improve the smell and taste, for example peppermint oil and eucalyptus oil, and sweeteners, for example saccharin. The abovementioned pharmaceutical formulations can also contain other pharmaceutical active compounds in addition to the compounds according to the present invention. The abovementioned pharmaceutical formulations are prepared in the customary manner by known methods, for example by mixing the active compound or compounds with the excipient or excipients.

The therapeutically active compounds should preferably be present in the abovementioned pharmaceutical formulations in a concentration of about 0.1 to 99.5, preferably about 0.5 to 95% by weight of the total mixture.

The formulations mentioned can be used on humans and animals orally, rectally, parenterally (intravenously, intramuscularly or subcutaneously), intracisternally, intravaginally, intraperitoneally or locally (dusting powder, ointment, drops) and for the therapy of infections in hollow spaces and body cavities. Possible suitable formulations are injection solutions, solutions and suspensions for oral therapy and gels, infusiton formulations, emulsions, ointments or drops, ophthalmological and dermatological formulations, silver salts and other salts, eardrops, eye onintments, dusting powders or solutions can be used for local therapy. In the case of animals, intake can also be in suitable formulations via the feed or drinking water. Gels, powders, dusting powders, tablets, delayed release tablets, premixes, concentrates, granules, pellets, boli, capsules, aerosols, sprays and inhalants can furthermore be used on humans and animals. The compounds according to the present invention can moreover be incorporated into other carrier materials, such as for example, plastics (chain of plastic for local therapy), collagen or bone cement.

In general, it has proved advantageous both in human and in veterinary medicine to administer the active compound or compounds according to the present invention in total amounts of about 0.1 to about 2 mg/kg, preferably 0.5 to 1 mg/kg of body weight, 1–3 times every 24 hours, if appropriate in the form of several individual doses, to achieve the desired results. However, it may be necessary to deviate from the dosages mentioned, and in particular to do so as a function of the nature and body weight of the object to be treated, the nature and severity of the disease, the nature of the formulation and of the administration of the medicament and the period or interval within which administration takes place. Thus in some cases it can suffice to manage with less than the abovementioned amount of active compound, while in other cases the abovementioned amount of active compound must be exceeded. The particular optimum dosage and mode of administration required for the active compounds can be determined by any expert on the basis of his expert knowledge.

EXAMPLES

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Synthesis of Oligonucleotide Represented by the SEQ. ID. NO: 1

In order to synthesize the peptide of the present invention represented by the SEQ. ID. NO: 2, we, the present inventors used Merrifield's liquid solid phase method in which Fmoc (9-fluorenylmethoxycarbonyl) was used as a protecting group (Merrifield, R. B., *J. Am. Chem. Soc.*, 1963, 85, 2149). For the peptide having —$NH_2$ type carboxyl terminal, rink amide MBHA-resin was used as a starting material. And, Fmoc-amino acid-Wang resin (SynPep Corporation) was used for the peptide having —OH type carboxyl terminal. The extension of peptide chain by Fmoc-amino acid coupling was performed by N-hydroxybenzo triazole (HOBt)-dicyclohexycarbodiimide (DCC) method. Particularly, Fmoc-amino acid of amino terminal of each peptide was coupled, and the Fmoc group was removed by using 20% piperidine/NMP (N-methyl pyrolidone) solution. After washing with NMP and DCM (dichoromethane), the peptide was dried with nitrogen gas. TAF (trifluoroacetic acid)-phenol-thioanisole-$H_2O$-triisopropylsilane (85: 5: 5: 2.5: 2.5 vol/vol) solution was added thereto. In order to remove protecting group and to separate peptide from resin, the peptide was reacted for 2–3 hours, and it was precipitated by using diethylether. The crude peptide was purified by using reverse phase(RP)-HPLC column(Delta Pak, $C_{18}$ 300 Å, 15, 19.0 mm ×30 cm, Waters) in acetonitrile gradient containing 0.05% TFA. Synthesized peptide was hydrolyzed with 6 N-HCl at 110° C., and the residues were vacuum concentrated. And then, its amino acid composition was analyzed with amino acid analyzer (Hitachi 8500 A) after dissolving in 0.02 N-HCl. As a result, the purity of the peptide was over 95%, and the molecular weight obtained by MALDI mass spectrometry (Hill, et al., *Rapid Commun. Mass Spectroinetry*, 1991, 5, 395) was the same as the molecular weight obtained by calculation of amino acids. Therefore, it was confirmed that the peptide having correct amino acid sequence was synthesized.

Experimental Example 1

Anti-bacterial Activity of the Peptides

<1-1> Measurement of MIC

In order to measure the anti-bacterial activity of the peptide synthesized in Example 1, minimum inhibitory concentration (MIC) of the peptide was measured.

The present inventors used *Bacillus subtilis* (KCTC 1918) and *Staphylococus epidermidis* (KCTC 1917) as Gram-positive bacteria, and *Pseudomonas aeruginosa* (KCTC 1637) and *Salmonella typhimurium* (KCTC 1926) as Gram-negative bacteria for this experiment. All the bacteria used in this experiment were given by Korea Research Institute of Bioscience and Biotechnology (KRIBB). Each bacterial strain was cultured in LB medium(1% bacto-trypton, 0.5% bacto-yeast extract, 1% sodium chloride) to the mid-log phase, and diluted with 1% bacto-peptone medium at the concentration of $1 \times 10^4$ cells/100 μl. The diluted bacteria were loaded into micro-titrate plate. Antibiotic peptide synthesized in Example 1 and CA-MA peptide (as a comparative group) were half-fold diluted consecutively from 25 μM/well, and added into the plate for culture at 37° C. for 6 hours. Finally, the MIC of each strain was determined by observing $OD_{620}$ with a micro-titrate plate reader. The results are described in Table 1.

TABLE 1

Anti-bacterial activity of peptides against Gram-positive and Gram-negative bacteria

| | MIC (μM) | | | |
| --- | --- | --- | --- | --- |
| | Gram-positive | | Gram-negative | |
| Peptide | B. subtilis | S. epidermidis | P. aeruginosa | S. typhimurium |
| CA-MA | 3.12 | 3.12 | 1.56 | 0.19 |
| Synthetic peptide (SEQ ID. NO: 2) | 0.78 | 1.56 | 0.78 | 0.097 |

As a result, it was confirmed that the antibiotic peptide of the present invention represented by the SEQ. ID. NO: 2 had around 4 times higher antibiotic activity than that of CA-MA peptide.

<1-2> Visualization of Anti-bacterial Activity

In order to visualize the antibiotic activity of the synthetic peptide of the present invention on the plate, *Pseudomonas aeruginosa* and *Bacillus subtilis* were inoculated in LB medium (1% bacto trypton, 0.5% yeast extract, 1% sodium chloride), and cultured to mid-log phase. Particularly, $4 \times 10^5$ *P. aeruginosa* cells were loaded into the medium, and 4 μM of synthetic peptide was added thereto. $4 \times 10^5$ *B. subtilis* cells were also loaded into the medium, and 1 μM of synthetic peptide was added thereto. After culturing for 2 hours at 37° C., the culture fluid was smeared on LB plate to visualize the cells. At this time, CA-MA peptide was used as a comparative group.

As a result, lots of colonies were found in positive control group (FIG. 1A), colonies were found to be a little grown in a group where CA-MA peptide was added (FIG. 1B) and no colony was found in a group where synthetic peptide of the present invention was added (FIG. 1C), meaning the peptide of the present invention could completely inhibit the growth of bacteria.

From the above results, it was confirmed that the synthetic peptide of the present invention represented by the SEQ. ID. NO: 2 had superior antibiotic activity to that of CA-MA peptide.

<1-3> Anti-bacterial Activity Observation with SEM

Anti-bacterial activity of the synthetic peptide of the present invention was observed with SEM (scanning electron microscopy). *Bacillus subtilis* (Gram-positive) and *Pseudomonas aeruginosa* (Gram-negative) cells were cultured in LB medium (1% bacto trypton, 0.5% bacto yeast extract, 1% sodium chloride) to mid-log phase, and the cells were diluted with 10 mM of Na-phosphate buffer containing 100 mM of NaCl at the concentration of $10^8$ cells/ml. Synthetic peptide of the present invention and CA-MA peptide (as a comparative group) were added into the diluted cell culture medium (final conc. 0.78 μM in *B. subtilis* culture, 1.56 μM in *P. aeruginosa* culture), followed by further culturing for 30 minutes at 37° C. 0.2 M Na-phosphate buffer containing 5% glutaraldehyde was added into the medium, and the cells were fixed for 2 hours at 4° C. The cells were filtered with isopore filters (0.2 μm pore size, Millipore, Bedford, Mass., USA), and washed with 0.1 M Na-cacodylate buffer (pH 7.4). The filters were treated with 1% osmium tertoxide and dehydrated. After freeze-drying and gold coating, the filters were observed with SEM (HITACHI S-2400, Japan).

As a result, when *B. subtilis* and *S. aeruginosa* were treated with the synthetic peptide of the present invention represented by the SEQ. ID. NO: 2, much more destroyed cells were observed than when in control and when the cells were treated with CA-MA peptide (FIG. 3 and FIG. 4).

<1-4> Measurement of Membrane Dynamic Condition

The present inventors performed the below experiment in order to investigate the dynamic condition of lipid membrane of bacteria cells treated with synthetic peptide of the present invention. Particularly, *B. subtilis* (Gram-positive) and *P. aeruginosa* (Gram-negative) were cultured to mid-log phase in LB medium (1% bacto trypton, 0.5% bacto yeast extract, 1% sodium chloride). And the antibiotic peptide of the present invention and CA-MA peptide (as a comparative group) were treated (6.25 μM~0.097 μM, half-fold diluted) thereto. Each strains were further cultured for 2 hours at 37° C. After fixing with 0.25% formaldehyde for 1 hour at room temperature, cultured cells were washed with PBS (pH 7.4), and then frozen in liquid nitrogen. For the fluorescent labeling, PBS (pH 7.4) was added until $OD_{450}$ reached to 0.25, and DPH (1,6-diphenyl-1,3,5-hexatriene) dissolved in tetrahydrofuran was added (final conc. $10^4$ M), followed by further culturing for 45 minutes at 37° C. Steady-state fluorescence anisotropy was determined by measuring the strength of fluorescence with spectrofluorometer (HITACHI F-3010, Tokyo, Japan) at 330 nm and 450 nm.

Figure 5:
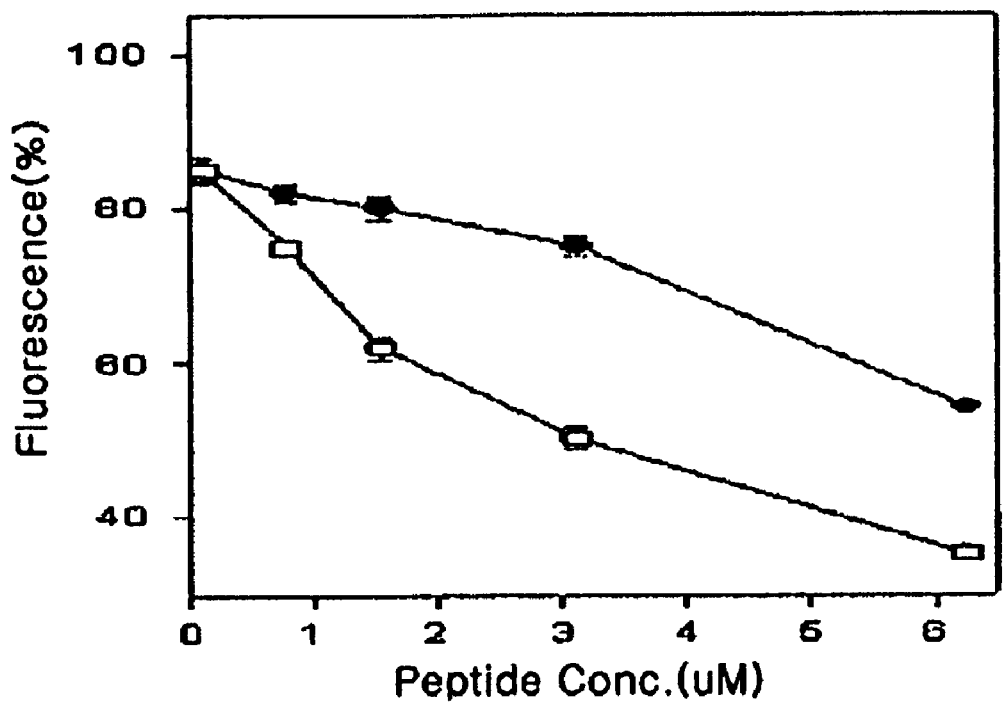
FIG. 5 is graphs showing the dynamic condition of lipid membrane after treating synthetic peptide of the present invention to *Bacillus subtilis* and *Pseudomonas aeruginosa*, A: Dynamic condition of lipid membrane of *Bacillus subtilis*, B: Dynamic condition of lipid membrane of *Pseudomonas aeruginosa*, ●CA-MA peptide, ☐: Synthetic peptide represented by the SEQ. ID. NO: 2
Figure 5:
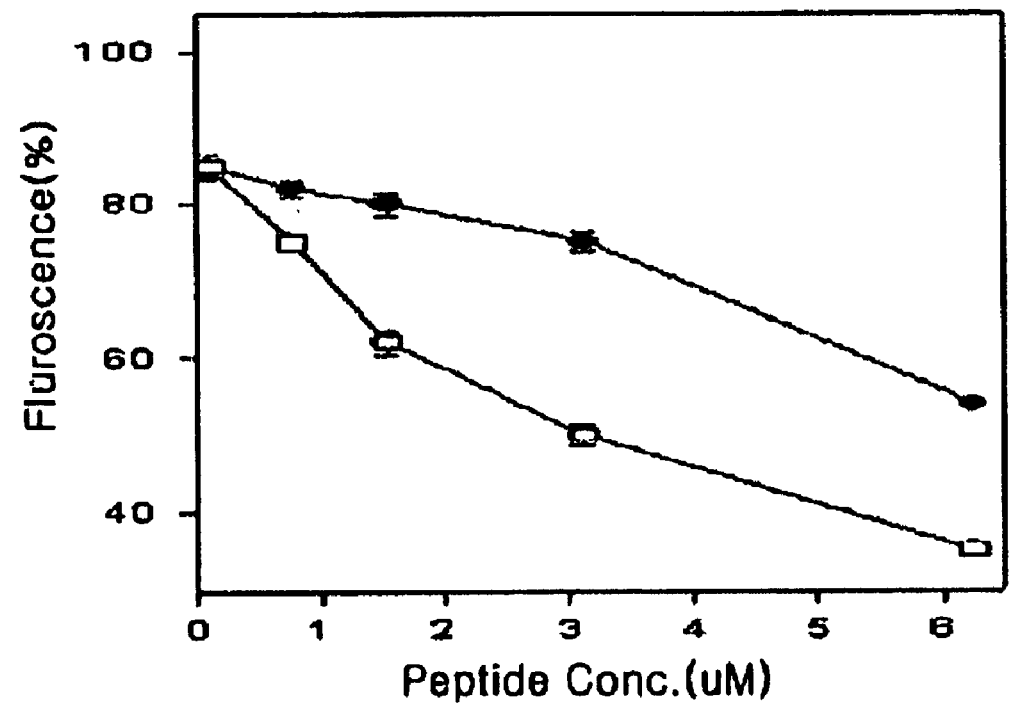

As a result, when *Bacillus subtilis* and *Pseudomonas aeruginosa* were treated with the synthetic peptide of the present invention represented by the SEQ. ID. NO: 2, DPH-labeled fluorescent materials were intercalated 15–20% lower position of membrane comparing to when the cells were treated with CA-MA peptide (FIG. 5).

Experimental Example 2

Anti-fungal Activity of Synthetic Peptide

<2-1> MTT Assay

In order to measure the anti-fungal activity of the synthetic peptide of the present invention, the present inventors performed MTT assay with *Candida albicans* (TIMM 1768) and *Tricosphoron beigelil* (KCTC 7707). Particularly, PDB medium (20% potato infusion frum, 2% bacto dextrose) containing various fungi was loaded into the wells (100 μl/well) of 96-well plate. Antibiotic peptides of the present invention and CA-MA peptide (as a comparative group) were half-fold diluted consecutively, and added into the plate for further culturing. 10 μl of MTT solution (3-[4,5-dimethyl-2-thiazolyl-2-thiazolyl]-2,5-diphenyl-2H-tetrazolium bromide, 5 mg/ml) was added into each well followed by further culturing for 5–6 hours. Formazan produced by mitochondria enzymes of living cells was dissolved in 100 μl of 0.04 N HCl-isopropanol. Finally, $OD_{570}$ was measured by using ELISA reader to determine the degree of MIC. The result was described in Table 2.

TABLE 2

Anti-fungal activity of peptides

| Peptide | MIC ($\mu$M) | |
|---|---|---|
| | C. albicans | T. beigelii |
| CA-MA | 12.5 | 6.25 |
| Synthetic peptide | 6.25 | 3.25 |

As a result, it was confirmed that the anti-fungal activity of the synthetic peptide of the present invention represented by the SEQ. ID. NO: 2 was about 2 times higher than that of CA-MA peptide.

Experimental Example 3

Anticancer Activity of Antibiotic Peptide

In order to measure the anticancer activity of the synthetic peptide of the present invention, the present inventors performed MTT assay with Calu-6 (a human lung cancer cell line), SNU 601 (a human stomach cancer cell line) and Jurkat (a T-cell lymphoma cell line) cells. Firstly, 90 $\mu$l of each cell line ($2\times10^5$ cells/ml) was loaded into each well of 96-well plate. At this time, only medium contained wells were used as a control. After shaking well, the cells were cultured in $CO_2$ incubator for 3 days. Formazan produced by mitochondria enzymes of living cells was dissolved in 100 $\mu$l of 0.04 N HCl-isopropanol, and finally, $OD_{540}$ was measured by using ELISA reader. The anti-cancer activity of antibiotic peptide of the present invention was represented by a percentage (OD of synthetic peptide treated well/OD of control×100).

Figure 6:
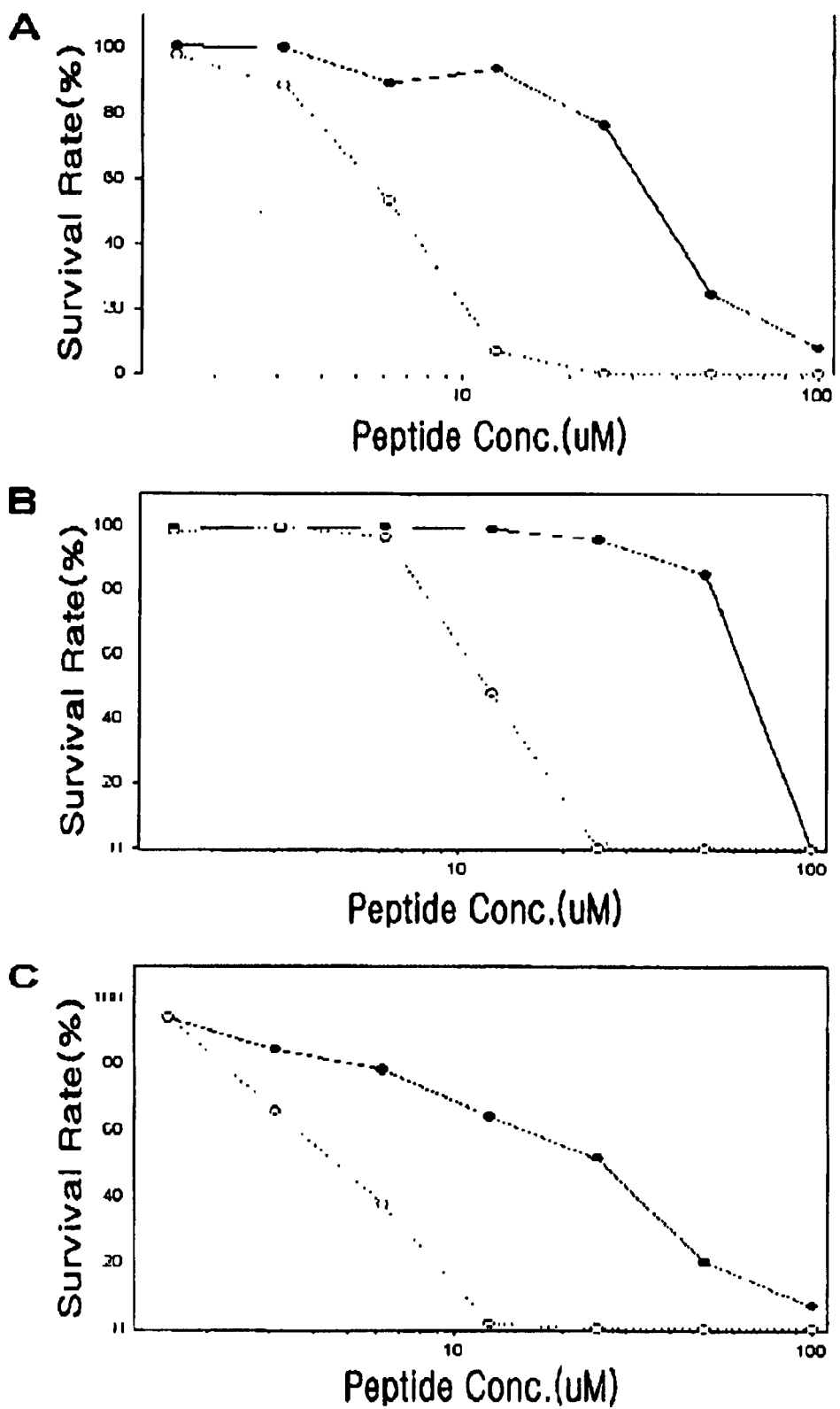
FIG. 6 is graphs showing the anticancer activity of the synthetic peptide of the present invention against various cancer cell lines.

As shown in FIG. 6, it was confirmed that the anti-cancer activity of the synthetic peptide of the present invention was higher than that of CA-MA peptide in all cell lines. To the concentration of 1 $\mu$M, synthetic peptide of the present invention did not showed anti-cancer activity. However, as concentration increases, the rapidly growing anticancer activity was detected. For example, strong anticancer activity which made complete restrain of cancer cell growth was observed with over 10 $\mu$M concentration.

Experimental Example 4

Cytotoxicity of Synthetic Peptide

In order to confirm if the synthetic peptide of the present invention showed cytotoxicity, hemolysis capacity of the synthetic peptide was investigated.

Human red blood corpuscles were diluted with PBS (pH 7.0) to the concentration of 8%, and loaded into each wells of 96-well plate. Synthetic peptide of the present invention was half-fold diluted consecutively from 12.5 $\mu$M/well, followed by reacting with the red blood corpuscles for 1 hour at 37° C. After centrifugation, $OD_{414}$ was measured to determine the amount of hemoglobin in the supernatant. At this time, CA-MA peptide was used as a comparative group and melittin was used as a positive control. In order to investigate the level of hemolysis, 1% triton X-100 was added, and then OD was measured. Hemolysis capacity of triton X-100 was regarded as 100%, with which hemolysis capacity of the synthetic peptide was compared and calculated according to the below <Mathematical Formula 1>.

<Mathematical Formula 1>

% hemolysis=(OD A−OD B/OD C−OD B)×100

In the above <Mathematical Formula 1>,

OD A=$OD_{414}$ of peptide solution,

OD B=$OD_{414}$ of PBS,

OB C=$OB_{414}$ of 1% triton X-100.

The results were described in Table 3.

TABLE 3

Cytotoxicity of peptides

| Peptide | % hemolysis ($\mu$M) | | | | | | | |
|---|---|---|---|---|---|---|---|---|
| | 12.5 | 6.25 | 3.125 | 1.56 | 0.78 | 0.39 | 0.195 | 0.097 |
| CA-MA | 0 | 0 | 0 | 0 | 0 | 0 | 0 | 0 |
| Synthetic Peptide (SEQ. ID. NO: 2) | 0 | 0 | 0 | 0 | 0 | 0 | 0 | 0 |
| Melittin | 100 | 100 | 95 | 93 | 31 | 0 | 0 | 0 |

As a result, while the bee venom, melittin, showed high cytotoxicity, CA-MA peptide and synthetic peptide of the present invention represented by the SEQ. ID. NO: 2 did not show any cytotoxicity.

Experimental Example 5

Acute Toxicity Test in Rat Via Non-oral Administration

The following experiments were performed to see if the synthetic peptide of the present invention has acute toxicity in rat.

6-week old SPF SD line rats were used in the tests for acute toxicity. Synthetic peptide of the present invention represented by the SEQ. ID. NO: 2 was suspended in 0.5% methyl cellulose solution and intravenous injected once to 2 rats per group at the dosage of 1 g/kg/15 ml. Death, clinical symptoms, and weight change in rats were observed, hematological tests and biochemical tests of blood were performed, and any abnormal signs in the gastrointestinal organs of chest and abdomen were checked with eyes during autopsy. The results showed that the synthetic peptide of the present invention did not cause any specific clinical symptoms, weight change, or death in rats. No change was observed in hematological tests, biochemical tests of blood, and autopsy. Therefore, the synthetic peptide used in this experiment are evaluated to be safe substances since they do not cause any toxic change in rats up to the level of 10 mg/kg in rats.

INDUSTRIAL APPLICABILITY

As shown above, the synthetic peptides and their derivatives of the present invention represented by the SEQ. ID. NO: 2 have no cytotoxicity but have excellent anti-bacterial, anti-fungal and anticancer activity, leading in an effective use thereof as a safe anticancer agent and antibiotics.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A modified cecropin A-magainin 2 peptide comprising a peptide of SEQ ID NO: 2.

2. An anti-bacterial or anti-fungal composition comparing the modified cecropin A-magainin 2 of claim 1.

3. The anti-bacterial or anti-fungal composition of claim 2 prepared in a form selected from the group consisting of tablets, coated tablets, capsules, pills, granules, suppositories, solutions, suspensions, emulsions, pastes, ointments, gels, creams, lotions, dusting powders and sprays.

4. The anti-bacterial or anti-fungal agent composition of claim 2 comprising the modified cecropin A-magainin 2 peptide in a concentration ranging from about 0.1 to 99.5 by weight of the total mixture.

5. An anti-cancer composition comprising a modified cecropin A-magainin 2 peptide of claim 1.

6. The anti-cancer composition of claim 5 prepared in a form selected from the group consisting of tablets, cooled tablets, capsules, pills, granules, suppositories, solutions, suspensions, emulsions, pastes, ointments, gels, creams, lotions, dusting powders and sprays.

7. The anti-cancer composition of claim 5 comprising the modified cecropin A-magainin 2 peptide in a concentration ranging from about 0.1 to 99.5 by weight of the total mixture.

* * * * *